(12) United States Patent
Klasen-Memmer et al.

(10) Patent No.: US 6,740,369 B2
(45) Date of Patent: May 25, 2004

(54) LIQUID-CRYSTALLINE MEDIUM

(75) Inventors: Melanie Klasen-Memmer, Heuchelheim (DE); Malgorzata Rillich, Darmstadt (DE); Volker Reiffenrath, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 84 days.

(21) Appl. No.: 10/206,978

(22) Filed: Jul. 30, 2002

(65) Prior Publication Data

US 2003/0071244 A1 Apr. 17, 2003

(30) Foreign Application Priority Data

Jul. 31, 2001 (DE) .......................... 101 37 319

(51) Int. Cl.$^7$ .................. C09K 19/12; C09K 19/30; C09K 19/20
(52) U.S. Cl. .............. 428/1.1; 252/299.63; 252/299.66; 252/299.67
(58) Field of Search ....................... 428/1.1; 252/299.63, 252/299.67, 299.66

(56) References Cited

U.S. PATENT DOCUMENTS

2003/0098443 A1 * 5/2003 Manabe et al. ........ 252/299.66
2003/0222245 A1 * 12/2003 Klasen-Memmer et al. ..... 252/299.66
2003/0228426 A1 * 12/2003 Heckmeier et al. .......... 428/1.1

FOREIGN PATENT DOCUMENTS

| DE | 2 209 127 | 9/1973 |
|---|---|---|
| DE | 2 240 864 | 2/1974 |
| DE | 2 338 281 | 2/1974 |
| DE | 2 321 632 | 11/1974 |
| DE | 24 50 088 | 4/1976 |
| DE | 26 37 430 | 2/1978 |
| DE | 28 53 728 | 7/1980 |
| EP | 0 240 379 | 10/1987 |
| JP | 9-208503 | 8/1997 |

OTHER PUBLICATIONS

English translation for JP 09–208,503 by computer, http://www6.ipdl.jpo.go.jp/Tokujitu/PAJdetail.ipdl?N0000=80&N0120=01&N2001=2&N3001=H09–208503.*

* cited by examiner

Primary Examiner—Shean C. Wu
(74) Attorney, Agent, or Firm—Millen, White, Zelano, Branigan, P.C.

(57) ABSTRACT

Liquid-crystalline mediums based on a mixture of polar compounds of negative dielectric anisotropy, comprising one or more compounds of the general formula I,

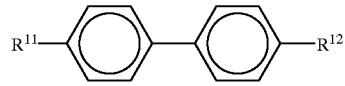

I in which $R^{11}$ is an alkyl group having from 1 to 12 carbon atoms or an alkenyl group having from 2 to 12 carbon atoms, and $R^{12}$ is an alkenyl group having from 2 to 12 carbon atoms, are useful for electro-optical display elements such as active matrix addressed displays which operate on the ECB and/or VA principles.

23 Claims, No Drawings

LIQUID-CRYSTALLINE MEDIUM

The present invention relates to a liquid-crystalline medium based on a mixture of polar compounds of negative dielectric anisotropy, and to the use thereof for electro-optical purposes and to displays containing this medium, in particular displays with active-matrix addressing based on the ECB effect and especially on the vertically aligned (VA) effect.

Matrix liquid-crystal (MLC)displays of this type are known. Non-linear elements which can be used for individual switching of the individual pixels are, for example, active elements (i.e., transistors). The term "active matrix" is then used, where a distinction can be made between two types.

1. MOS (metal oxide semiconductor) or other diodes on a silicon wafer as substrate.
2. Thin-film transistors (TFTs) on a glass plate as substrate.

The use of single-crystal silicon as substrate material restricts the display size, since even modular assembly of various part-displays results in problems at the joints, which is why type 2 is preferred. A distinction is made between two technologies: TFTs comprising compound semiconductors, such as, for example, CdSe, or TFTs based on polycrystalline or amorphous silicon. TFT displays usually operate as TN cells with crossed polarisers in transmission and are back-lit.

The term MLC displays here covers any matrix display with integrated non-linear elements, i.e., besides the active matrix, also displays with passive elements, such as varistors or diodes (MIM=metal-insulator-metal).

In liquid-crystal displays of this type, the liquid crystals are used as dielectrics, whose optical properties change reversibly on application of an electric voltage. Electro-optical displays which use liquid crystals as media are known to the person skilled in the art. These liquid-crystal displays use various electro-optical effects.

The principle of electrically controlled birefringence, the ECB ("electrically controlled birefringence") effect or DAP ("deformation of aligned phases") effect, was described for the first time in 1971 (M. F. Schieckel and K. Fahrenschon, "Deformation of nematic liquid crystals with vertical orientation in electrical fields", Appl. Phys. Lett. 19 (1971), 3912). This was followed by papers by J. F. Kahn (Appl. Phys. Left. 20 (1972), 1193) and G. Labrunie and J. Robert (J. Appl. Phys. 44 (1973), 4869).

The papers by J. Robert and F. Clerc (SID 80 Digest Techn. Papers (1980), 30), J. Duchene (Displays 7 (1986), 3) and H. Schad (SID 82 Digest Techn. Papers (1982), 244) have shown that liquid-crystalline phases must have high values for the ratio of the elastic constants $K_{33}/K_{11}$, high values for the optical anisotropy $\Delta n$, and values for the dielectric anisotropy $\Delta\epsilon$ of from about −0.5 to about −5 in order to be suitable for high-information display elements based on the ECB effect. Electro-optical display elements based on the ECB effect have a homeotropic edge alignment.

However, liquid-crystal displays of this type have some disadvantages compared with the known active-matrix TN displays, in particular a high viewing-angle dependence of the contrast ratio and of the grey shades.

A more recent variant of the ECB displays is the active matrix display based on the VAN (vertically aligned nematic) effect and the VAC (vertically aligned cholesteric) effect. VAN displays have been described, inter alia, in S. Yamauchi et al., SID Digest of Technical Papers, pp. 378 ff (1989), and VAC displays have been described in K. A. Crabdall et al., Appl.Phys.Lett. 65, 4 (1994).

The more recent VAN and VAC displays, like the ECB displays already disclosed earlier, contain a layer of a liquid-crystalline medium between two transparent electrodes, the liquid-crystal medium having a negative value for the dielectric constant anisotropy $\Delta\epsilon$. The molecules of this liquid-crystal layer have a homeotropic or tilted homeotropic alignment (i.e. substantially perpendicular to the electrode surfaces) in the switched-off state. Owing to the negative $\Delta\epsilon$, realignment of the liquid-crystal molecular parallel to the electrode surfaces takes place in the switched-on state.

In contrast to conventional ECB displays, in which the liquid-crystal molecules have, in the switched-on state, a parallel alignment with a preferential direction which is uniform over the entire liquid-crystal cell, in VAN and VAC displays this uniform parallel alignment is restricted only to small domains within the cell. Disclinations exist between these domains, also known as tilt domains.

As a consequence of this, VAN and VAC displays have greater viewing-angle independence of the contrast and of the grey shades compared with conventional ECB displays. In addition, displays of this type are simpler to produce since additional treatment of the electrode surface for uniform alignment of the molecules in the switched-on state, such as, for example, by rubbing, is no longer necessary.

In contrast to VAN displays, the liquid-crystal media in VAC displays additionally comprise one or more chiral compounds, such as, for example, chiral dopants, which, in the switched-on state, induce a helical twist of the liquid-molecules in the liquid-crystal layer by an angle of between 0 and 360°. The twist angle in the preferred case is about 90°.

Also known are liquid-crystal display elements using the IPS effect (in plane switching), in which both dielectrically positive and dielectrically negative liquid-crystal media can be used. Likewise, the dyes in guest/host displays can be employed either in dielectrically positive or dielectrically negative media, depending on the display mode used.

A further type of liquid-crystal display in which dielectrically negative media are used are the so-called "axially symmetric microdomain" (ASM for short) displays, which are preferably addressed by means of plasma arrays (PALCDs, from "plasma-addressed liquid-crystal displays").

The above-mentioned display elements, in particular those which operate on the VA effect, generally have relatively short response times. However, there is an increasing demand, in particular in TV and video applications, for displays having even shorter response times. This can in principle be achieved either by reducing the rotational viscosities or by reducing the layer thickness d in the display elements. In order to keep the d·$\Delta n$ value in the required range, liquid-crystal media having higher values of the optical anisotropy $\Delta n$ are therefore necessary for display elements having smaller layer thicknesses d.

In addition, the chemical resistance to moisture, air and physical influences, such as heat, radiation in the infrared, visible and ultraviolet region, as well as direct and alternating electric fields is important. Furthermore, LC (liquid crystal) phases which can be used industrially are required to have a liquid-crystalline mesophase in a suitable temperature range, low viscosity and the highest possible value for the voltage holding ratio.

An object of the invention is to provide a liquid-crystalline medium based on a mixture of polar compounds of negative dielectric anisotropy which at least substantially meets the above-mentioned requirements, in particular has low rotational viscosities and/or comparatively high values of the optical anisotropy Δn.

Upon further study of the specification and appended claims, further objects and advantages of this invention will become apparent to those skilled in the art.

It has now been found that these objects can be achieved if media according to the invention are used in displays.

The invention thus relates to a liquid-crystalline medium based on a mixture of polar compounds of negative dielectric anisotropy, characterised in that it comprises one or more compounds of the general formula I

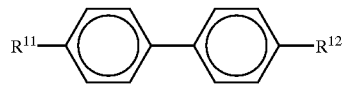

I in which
R$^{11}$ is an alkyl group having from 1 to 12 carbon atoms or an alkenyl group having from 2 to 12 carbon atoms, and
R$^{12}$ is an alkenyl group having from 2 to 12 carbon atoms.

Compounds of the formula I in which R$^{11}$ is C$_{1-10}$-alkyl and R$^{12}$ is 3-butenyl are described in JP 09208503 A as components of liquid-crystalline mixtures having only positive values of the dielectric anisotropy.

Preferably the concentration of dielectrically positive compounds in the mixture is 0% to 25%, more preferably 0% to 10%, and in particular 5% or less. In a preferred embodiment the mixtures do not contain any dielectrically positive compounds at all, at least only less than or equal to 1%.

Preferably the polar compounds of the mixture comprise one or more compounds with a terminal fluorine and/or one or more compounds with a fluorinated terminal group, e.g., OCF$_3$ or OCHF$_2$.

It has now been found, entirely unexpectedly, that the compounds of the formula I are very advantageously suitable as components in liquid-crystalline media based on a mixture of polar compounds of negative dielectric anisotropy. Thus, the use of one or more compounds of the formula I enables comparatively high values of the optical anisotropy Δn to be achieved without the rotational viscosity values being impaired. In addition, it is generally possible to achieve even lower rotational viscosities.

Furthermore, use of one or more compounds of the formula I enables mixtures having a broad liquid-crystalline mesophase range in a suitable temperature range, low viscosity and comparatively high values for the voltage holding ratio (HR) to be achieved.

The compounds of the formula I themselves are stable to moisture, air and physical influences, such as heat, radiation in the infrared, visible and ultraviolet region, as well as direct and alternating electric fields.

The media according to the invention exhibit very high HR values, low threshold voltages and in particular very good low-temperature stabilities at the same time as high clearing points.

The liquid-crystalline media according to the invention are advantageously suitable for use in liquid-crystal matrix display elements in which liquid-crystal mixtures of negative dielectric anisotropy (Δε<0) are employed. These are, in particular, display elements which operate on the principles mentioned at the outset, such as the ECB and VA principles, including vertically aligned nematics (VAN), vertically aligned cholesterics (VAC), multi-domain vertically aligned (MVA), and patterned vertically aligned (PVA) modes.

Furthermore, the media according to the invention can also advantageously be employed in ASM and PALC displays and displays operating on the IPS effect. Their use is also possible in guest/host displays. Preference is given here to MLC displays having an actively addressed matrix, in particular TFT displays.

The invention therefore furthermore relates to an electro-optical display element which contains, as dielectric, a liquid-crystalline medium according to the invention. Preference is given to those which operate in accordance with the ECB principle, in particular the VA principle. Actively addressed display elements are particularly advantageous here.

Preferred embodiments are given below:

The meaning of R$^{11}$ in the formula I includes straight-chain and branched alkyl having from 1 to 12 carbon atoms, preferably having from 1 to 7 carbon atoms. The alkyl radical is preferably straight-chain, and R$^{11}$ is therefore preferably methyl, ethyl, propyl, butyl, pentyl, hexyl or heptyl. R$^{11}$ may furthermore also be octyl, nonyl, decyl, undecyl or dodecyl. R$^{11}$ is very particularly preferably methyl, ethyl, propyl, butyl or pentyl, in particular methyl.

The meaning of R$^{12}$ and/or R$^{11}$ in the formula I includes straight-chain and branched alkenyl having from 2 to 12 carbon atoms, preferably having from 2 to 5 carbon atoms. Straight-chain alkenyl groups are preferred. Preference is furthermore given to C$_2$–C$_7$-1E-alkenyl, C$_4$–C$_7$-3E-alkenyl, C$_5$–C$_7$-4-alkenyl, C$_6$–C$_7$-5-alkenyl and C$_7$-6-alkenyl, in particular C$_2$–C$_7$-1E-alkenyl, C$_4$–C$_7$-3E-alkenyl and C$_5$–C$_7$-4-alkenyl. Particularly preferred meanings of R$^{12}$ are vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl or oct-1-, -2-, -3-, -4-, -5-, -6- or -7-enyl. Of these, the 3-alkenyls, in particular but-3-enyl and pent-3-enyl, are very particularly preferred.

Very particularly preferred liquid-crystal mixtures according to the invention therefore comprise one or more compounds of the formulae Ia, Ib, Ic and/or Id

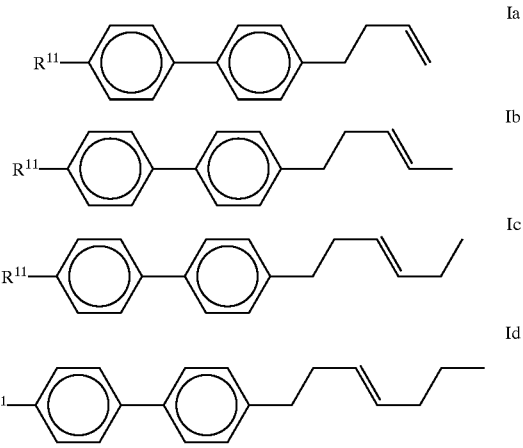

in which R$^{11}$ is as defined above, in particular is alkyl, preferably methyl, ethyl, propyl, butyl or pentyl, particularly preferably methyl.

Further preferred embodiments are given below:

a) Medium which additionally comprises one or more compounds of the formula II:

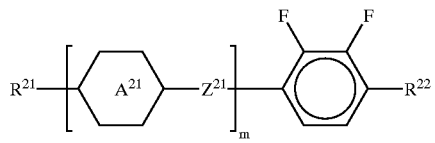

II in which
    m is 1 or 2,
    $Z^{21}$ is —COO— or a single bond, and
    $A^{21}$ is trans-1,4-cyclohexylene or 1,4-phenylene,
    $R^{21}$ and $R^{22}$, independently of one another, are an alkyl or alkenyl group having up to 12 carbon atoms, in which, in addition, one or more non-adjacent $CH_2$ groups may be replaced in each case by —O—, —S— or —C≡C—.

b) Medium which additionally comprises one or more compounds of the formula III:

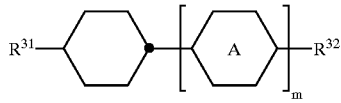

III in which
    m is 1 or 2,
    A is trans-1,4-cyclohexylene or 1,4-phenylene, in which one H atom may be replaced by F,
    $R^{31}$ and $R^{32}$, independently of one another, are an alkyl or alkenyl group having up to 12 carbon atoms, in which, in addition, one or more non-adjacent $CH_2$ groups may be replaced in each case by —O—, —S— or —C≡C—.

c) Medium which additionally comprises one or more compounds of the formula IV

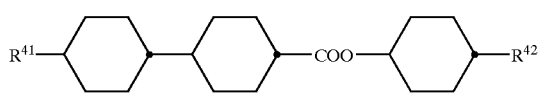

IV in which $R^{41}$ and $R^{42}$, independently of one another, are as defined for $R^{22}$.

d) Medium which additionally comprises one or more compounds of the formula VI

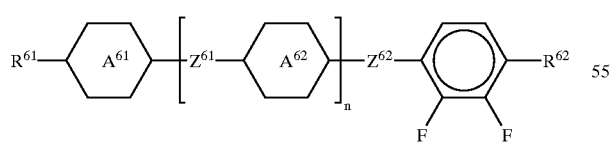

VI in which $R^{61}$ and $R^{62}$, independently of one another, are as defined for $R^{22}$, and

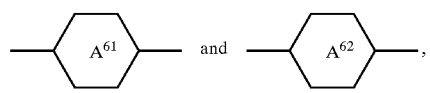

independently of one another, are

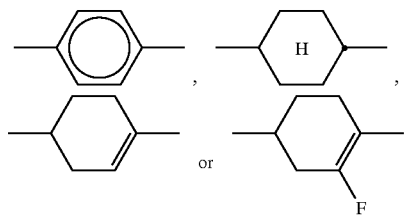

preferably, independently of one another, are (hexagon with H) or (phenyl ring), one of
    $Z^{61}$ and $Z^{62}$ is $OCF_2$ or $CF_2O$ and the other is a single bond, and
    n is 0 or 1.

e) Medium which additionally comprises one or more compounds of the formula VII

VII

R^{71}—(A^{71})—Z^{71}—(A^{72})—R^{72} in which
    $R^{71}$ and $R^{72}$ are each, independently of one another, as defined for $R^{22}$,
    $Z^{71}$ is —$CH_2CH_2$—, —CH=CH—, —COO— or a single bond, —(A^{71})—  and  —(A^{72})— are each, independently of one another,

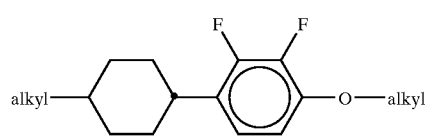

f) Medium which comprises one or more compounds selected from the formulae IIa to IIj:

IIa alkyl—(cyclohexyl)—(difluorophenyl)—O—alkyl

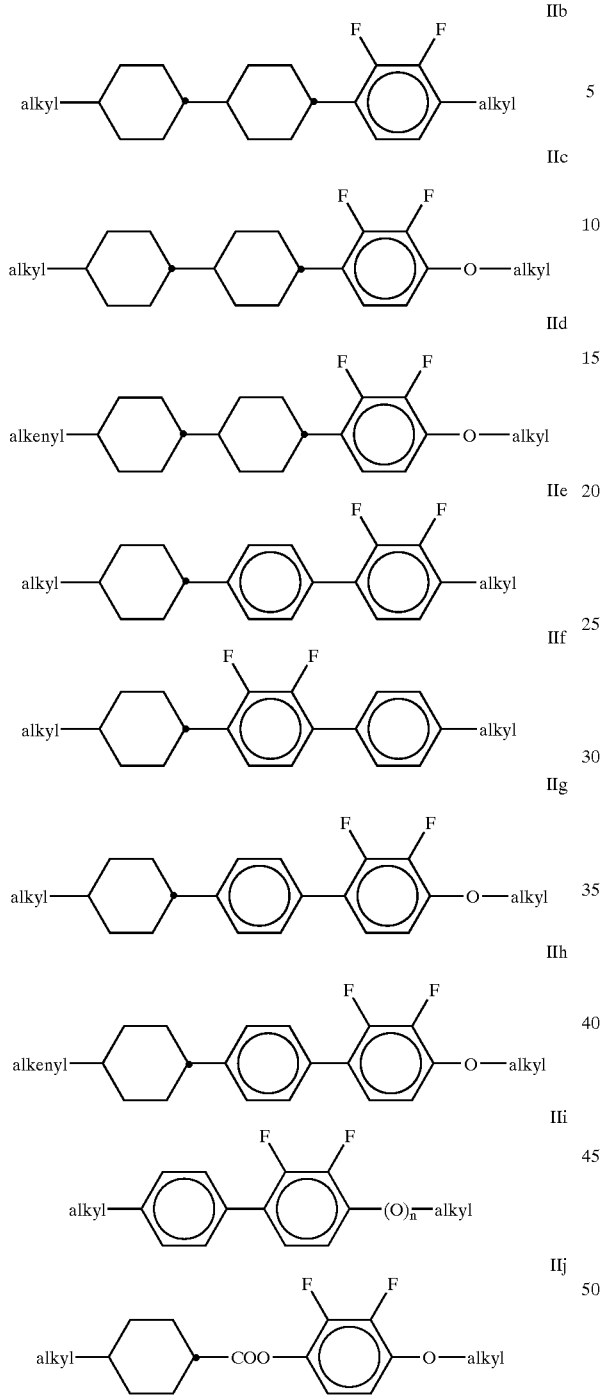

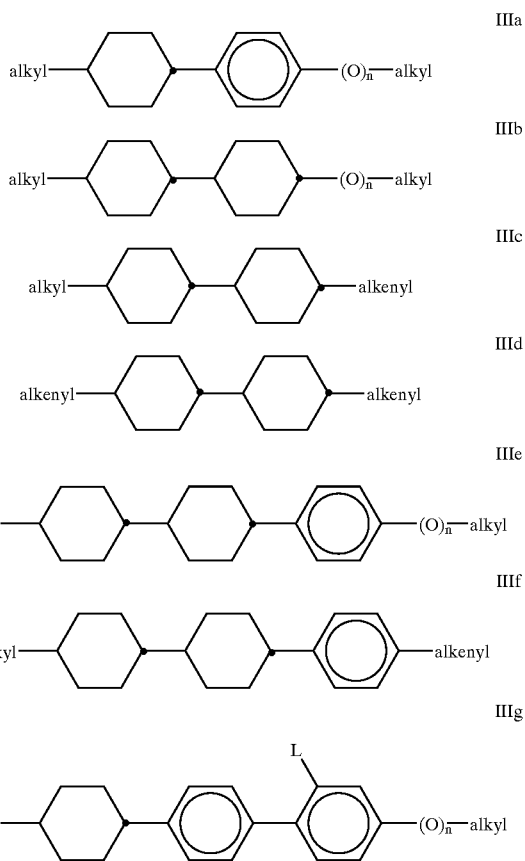

in which alkyl is in each case, independently of one another, a straight-chain alkyl group having from 1 to 6 carbon atoms, n is 0 or 1, and each alkenyl is a straight-chain alkenyl group having from 2 to 6 carbon atoms. Particular preference is given here to a medium having one or more compounds of the formulae IIa, IIb, IIc, IIg, IIi and/or IIj. In accordance with the invention, low rotational viscosities can be achieved, in particular, using media comprising compounds of the formula IIg. In addition, compounds of the formula IIi, in particular where n=1, can advantageously be employed in media of high optical anisotropy, in particular $\Delta n > 0.11$.

g) Medium which comprises one or more compounds selected from the formulae IIIa to IIIg:

in which alkyl is in each case, independently of one another, a straight-chain alkyl group having from 1 to 6 carbon atoms, alkenyl is a straight-chain alkenyl group having from 2 to 6 carbon atoms, n is 0 or 1, and L is H or F. Particular preference is given here to a medium having one or more compounds of the formulae IIIb, IIIc, IIIf and/or IIIg. In accordance with the invention, low rotational viscosities can be achieved, in particular, using media comprising compounds of the formula IIIc.

h) Medium which comprises one or more compounds selected from the formulae VIa to VIq:

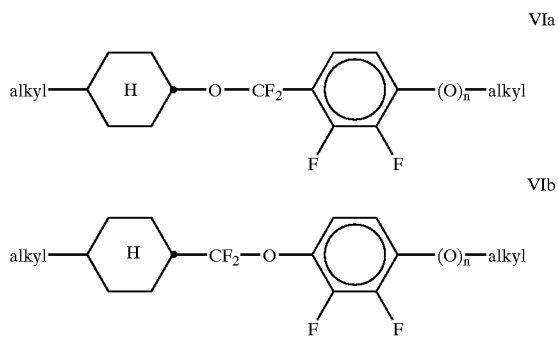

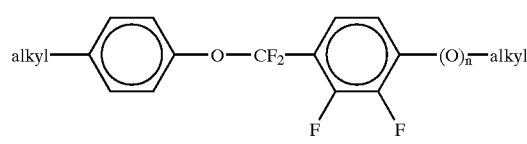

in which alkyl is in each case, independently of one another, a straight-chain alkyl group having from 1 to 6 carbon atoms, and n is 0 or 1.

i) Medium which comprises one or more compounds selected from the formulae VIIa to VIId:

in which $R^{71}$ and $R^{72}$ are each as defined above under the formula

VII. $R^{71}$ is preferably n-alkyl having from 1 to 5 carbon atoms, particularly preferably having from 1 to 3 carbon atoms, and $R^{72}$ is preferably n-alkyl or n-alkoxy having from 1 to 5 carbon atoms or alkenyl having from 2 to 5 carbon atoms.

k) Medium which comprises 1, 2 or 3 compounds of the formula I.

l) Medium which comprises at least one compound of the formula I and at least one compound of the formulae IId, IIf and/or IIIc.

m) Medium which consists essentially of at least one compound of the formula I, at least one compound of the formula II and at least one compound of the formula III.

n) Medium which consists essentially of at least one compound of the formula I, at least one compound of the formula II and at least one compound of the formula VI.

o) Medium which consists essentially of at least one compound of the formula I, at least one compound of the formula II and at least one compound of the formula VII.

p) Medium which comprises 2–35% by weight, preferably 2–25% by weight, particularly preferably 4–18% by weight, of one or more compounds of the formula I.

q) Medium which comprises 20–90% by weight, preferably 30–85% by weight, particularly preferably 40–80% by weight, of one or more compounds of the formula II.

r) Medium which comprises 5–60% by weight, preferably 10–40% by weight, of one or more compounds of the formula III.

s) Medium comprising
2–25% by weight of one or more compounds of the formula I,
30–85% by weight of one or more compounds of the formula II, and
10–40% by weight of one or more compounds of the formula III.

The liquid-crystal mixture preferably has a nematic phase range of at least 80 K, particularly preferably of at least 100 K, and a rotational viscosity of not greater than 300 mPa·s, in particular less than or equal to 250 mPa·s and particularly preferably not greater than 200 mPa·s, at 20° C.

The liquid-crystal mixture according to the invention has a dielectric anisotropy $\Delta\epsilon$ of preferably less than or equal to $-0.5$, more preferably less than or equal to $-2.0$, particularly preferably less than or equal to $-3.0$. A preferred range of values for $\Delta\epsilon$ is from about $-0.5$ to $-8$, in particular from about $-2.0$ to $-7.0$, particularly preferably from about $-3.0$ to $-5.5$, in each case determined at 20° C. and 1 kHz. The dielectric constant $\epsilon_{\|}$ is generally greater than or equal to 3, preferably from 3.2 to 4.5.

The birefringence $\Delta n$ in the liquid-crystal mixture generally has a value greater than 0.060, preferably greater than or equal to 0.075, particularly preferably greater than or equal to 0.090. Media of this type having comparatively high optical anisotropy generally have $\Delta n$ values of up to 0.14, with $\Delta n$ values of up to 0.17 or higher also being conceivable.

The dielectrics may also comprise further additives known to the person skilled in the art and described in the literature. For example, 0–15% by weight of pleochroic dyes may be added, furthermore conductive salts, preferably ethyldimethyldodecylammonium 4-hexyloxybenzoate, tetrabutyl-ammonium tetraphenylboranate or complex salts of crown ethers (cf., for example, Haller et al., Mol. Cryst. Liq. Cryst. 24, 249–258 (1973)) may be added in order to improve the conductivity, or substances may be added in order to modify the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the above-mentioned formulae of the liquid-crystal mixtures according to the invention are either known or their methods of preparation can easily be derived from the prior art by the person skilled in the relevant art since they are based on standard methods described in the literature.

The term "alkyl" in formulae II to VII includes straight-chain and branched alkyl having up to 12 carbon atoms, preferably from 1 to 7 carbon atoms, and is therefore, in particular, methyl, ethyl, propyl, butyl, pentyl, hexyl or pentyl. The meanings octyl, nonyl, decyl, undecyl and dodecyl are also possible.

The term "alkenyl" in formulae II to VII includes straight-chain and branched alkenyl having up to 12, preferably having from 2 to 7, carbon atoms. Straight-chain alkenyl groups are preferred. Further preferred are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4alkenyl.

Of these groups, particular preference is given to vinyl, 1 E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl and 6-heptenyl. alkenyl groups having up to 5 carbon atoms are particularly preferred.

The nematic liquid-crystal mixtures in the displays according to the invention generally comprise two components A and B, which themselves consist of one or more individual compounds.

Component A has significantly negative dielectric anisotropy and gives the nematic phase a dielectric anisotropy of $\leq -0.3$. It preferably comprises compounds of the formulae II and/or VI.

The proportion of component A is preferably between 45 and 100% by weight, in particular between 60 and 100% by weight.

For component A, one or more individual compounds which have a value of $\Delta\epsilon$ of $\leq -0.8$ are preferably selected. This value must be more negative the smaller the proportion of component A in the mixture as a whole.

Particularly preferred individual compounds of component B are extremely low-viscosity viscous nematic liquid crystals having a viscosity of not greater than 18 $mm^2 \cdot s^{-1}$, preferably not greater than 12 $mm^2 \cdot s^{-1}$ at 20° C.

Component B is monotropically or enantiotropically nematic, has no smectic phases and is able to prevent the occurrence of smectic phases down to very low temperatures in liquid-crystal mixtures. For example, if various materials of high nematogeneity are added to a smectic liquid-crystal mixture, the nematogeneity of these materials can be compared through the degree of suppression of smectic phases that is achieved. A multiplicity of suitable materials is known to the person skilled in the art from the literature. Particular preference is given to compounds of the formula II.

The liquid-crystal mixtures according to the invention preferably comprise from 4 to 25, in particular from 6 to 18, compounds of the formulae I, II and III, optionally additionally also of the formulae IV, VI and/or VII.

Besides the compounds of the formulae I, II and III, and optionally additionally of the formulae IV, VI and/or VII, other constituents may also be present, for example in an amount of up to 45% by weight of the mixture as a whole, but preferably up to a maximum of 35% by weight, in particular up to a maximum of 10% by weight.

The other constituents are preferably selected from nematic or nematogenic substances, in particular known substances, from the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1.4-biscyclohexylbiphenyls or cyclohexylpyrimidines, phenyl- or cyclohexyldioxanes, optionally halogenated stilbenes, benzyl phenyl ethers, tolans and substituted cinnamic acids.

The most important compounds which are suitable as constituents of liquid-crystal mixtures of this type can be characterised by the formula VIII $$R^a\text{—}L\text{—}G\text{—}E\text{—}R^b \qquad \text{VIII}$$

in which

L and E are each a carbocyclic or heterocyclic ring system from the group formed by 1.4-disubstituted benzene and cyclohexane rings, 4.4'-disubstituted biphenyl, phenylcyclohexane and cyclohexylcyclohexane systems, 2.5-disubstituted pyrimidine and 1.3-dioxane rings, 2.6-disubstituted naphthalene, di- and tetrahydronaphthalene, quinazoline and tetrahydroquinazoline, G is —CH=CH—   —N(O)=N—
—CH—CQ—   —CH=N(O)—
—C≡C—   —CH$_2$—CH$_2$—
—CO—O—   —CH$_2$—O—
—CO—S—   —CH$_2$—S—
—CH=N—   —COO-Phe-COO— or a C—C single bond,

Q is halogen, preferably chlorine, or —CN, and $R^a$ and $R^b$ are each alkyl, alkoxy, alkanoyloxy or alkoxycarbonyloxy having up to 18, preferably up to 8, carbon atoms, or one of these radicals is alternatively CN, NC, NO$_2$, CF$_3$, F, Cl or Br.

In most of these compounds, $R^a$ and $R^b$ are different from one another, one of these radicals usually being an alkyl or alkoxy group. Other variants of the proposed substituents are also common. Many such substances or also mixtures thereof are also commercially available. All these substances can be prepared by methods known from the literature.

It goes without saying to the person skilled in the art that the ECB mixture according to the invention may also comprise compounds in which, for example, H, N, O, Cl and F have been replaced by the corresponding isotopes.

The construction of the liquid-crystal displays according to the invention corresponds to the usual geometry, as described, for example, in EP-A 0 240 379.

Besides the compounds of the formula I, the mixtures according to the invention preferably comprise one or more compounds of the compounds mentioned below.

The following abbreviations are used: (n, m=1–6; z=1–6)

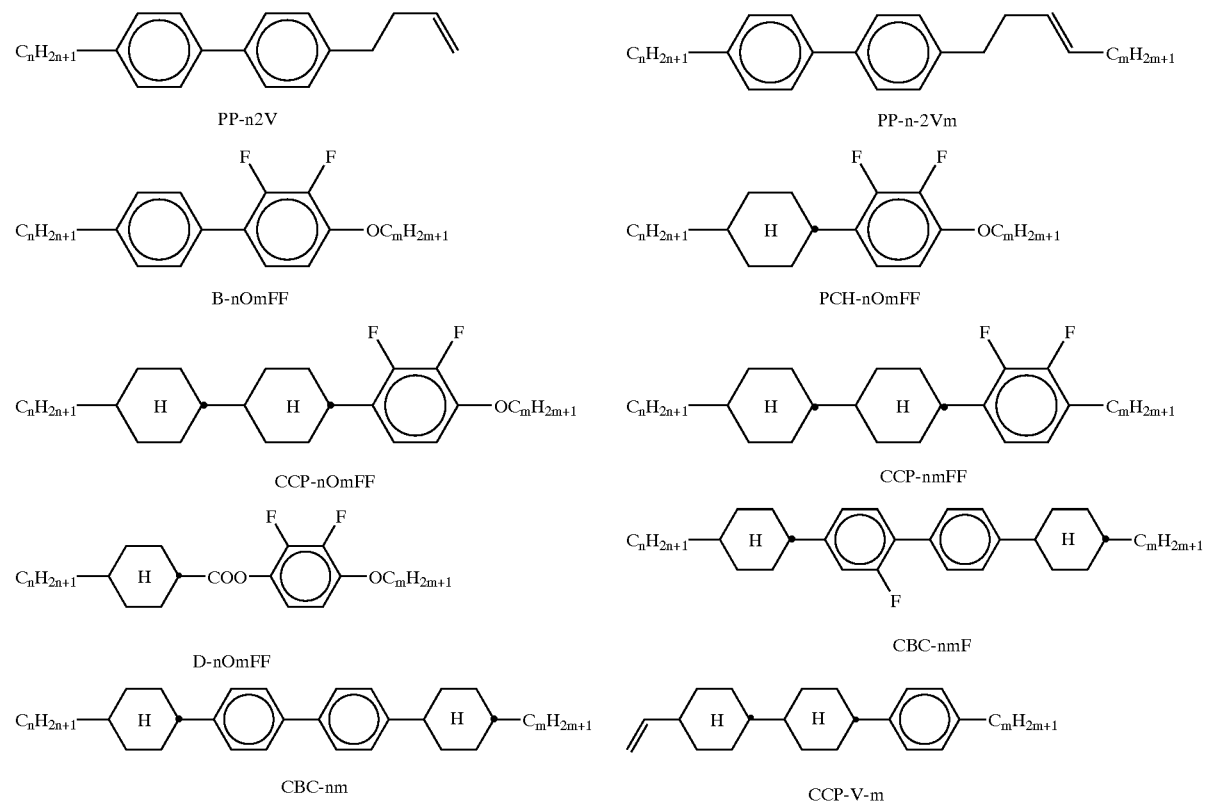

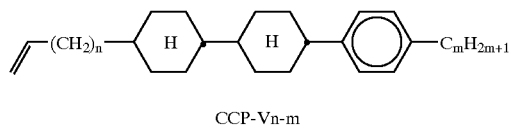
CCP-Vn-m
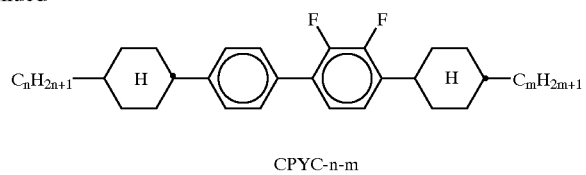
CPYC-n-m
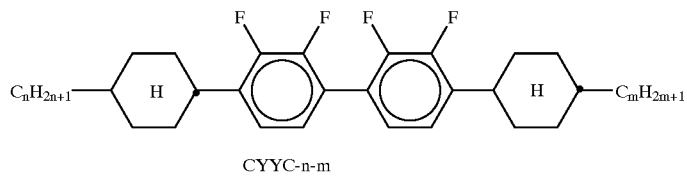
CYYC-n-m
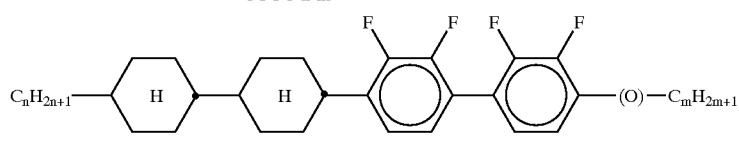
CCYY-n-(O)m
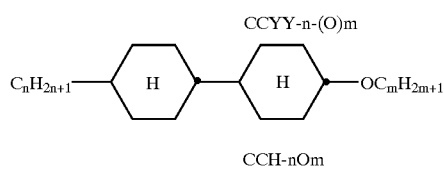
CCH-nOm
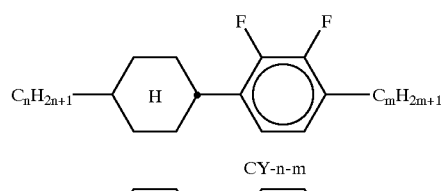
CY-n-m
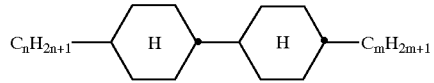
CCH-nm
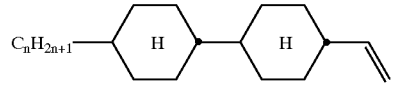
CC-n-V
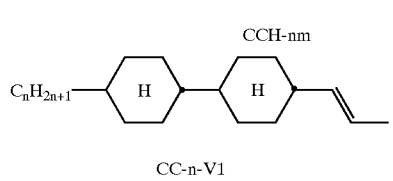
CC-n-V1
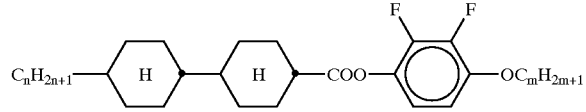
CP-nOmFF
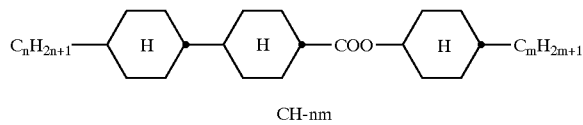
CH-nm
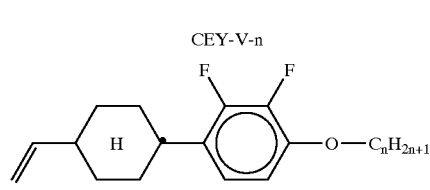
CEY-V-n
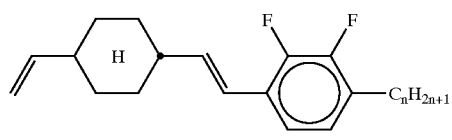
CVY-V-n
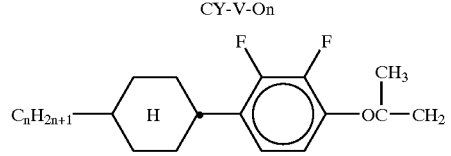
CY-V-On
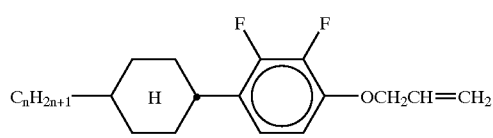
CY-n-O1V
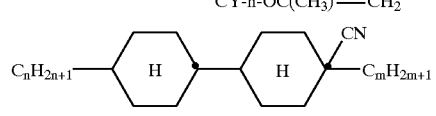
CY-n-OC(CH₃)=CH₂
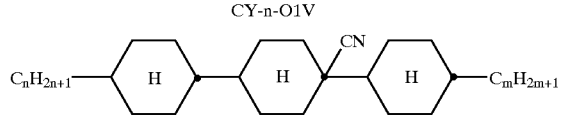
BCN-nm
CCN-nm

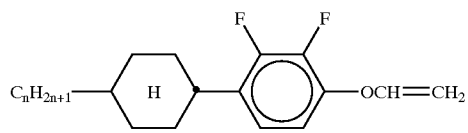
CY-nOV
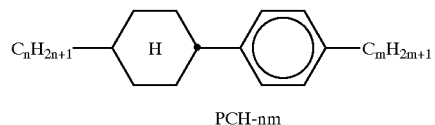
PCH-nm
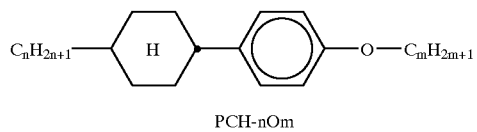
PCH-nOm
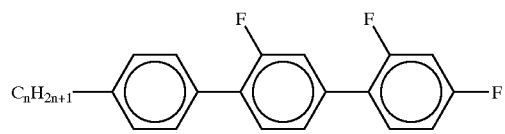
PGIGI-n-F
BCH-nm
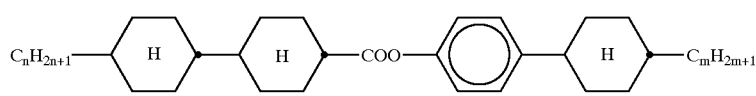
CCPC-nm
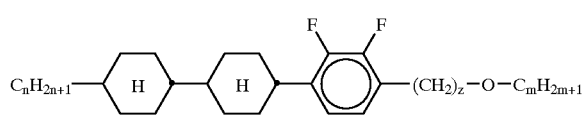
CCY-n-zOm
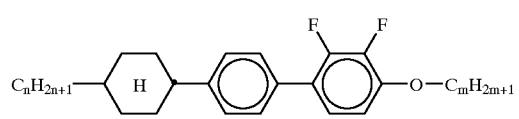
CPY-n-Om
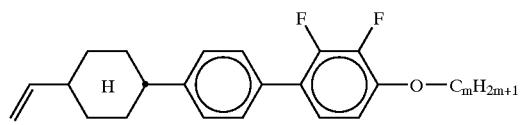
CPY-V-Om
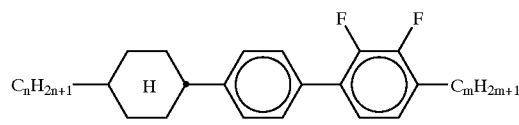
CPY-n-m
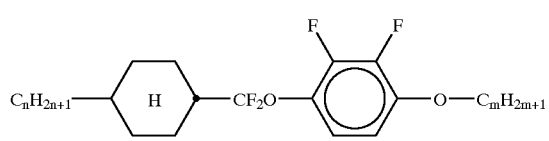
CQY-n-(O)m
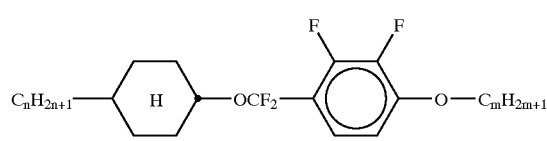
CQIY-n-(O)m
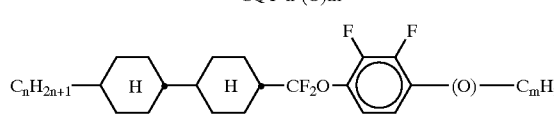
CCQY-n-(O)m
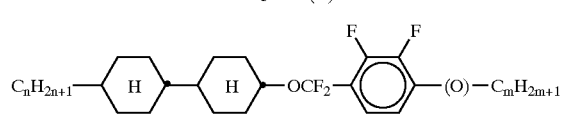
CCQIY-n-(O)m
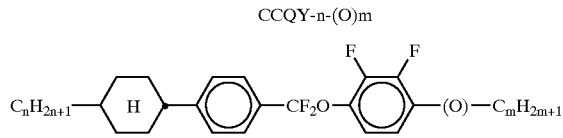
CPQY-n-(O)m
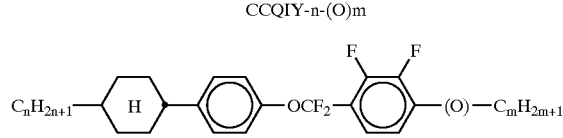
CPQIY-n-(O)m
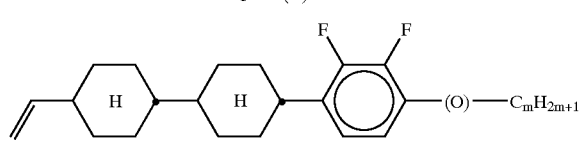
CCY-V-(O)m The following examples are intended to explain the invention without limiting it. Above and below, percentages are per cent by weight, unless stated otherwise; all temperatures are indicated in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The voltage values $V_0$ indicated are measured in a conventional ECB cell with a layer thickness of 20 μm at 20° C.

The following abbreviations are used:

T(N,I) clearing point [° C.],

Δn optical anisotropy (birefringence) at 20° C. and 589 nm, $n_e$ extraordinary refractive index, Δε dielectric anisotropy at 20° C. and 1 kHz, $\epsilon_\perp$ dielectric constant perpendicular to the longitudinal molecular axis at 20° C. and 1 kHz, $k_3/k_1$ ratio of the elastic constants $K_3$ and $K_1$, $\gamma_1$ rotational viscosity [mPa·s] (at 20° C., unless stated otherwise), $V_0$ Fredericksz threshold voltage [V], $t_{store}$ low-temperature storage stability in hours (−30° C., −40° C.).

EXAMPLE 1

| Compound/ abbreviation | Concentration/ % by weight | Physical properties |
| --- | --- | --- |
| PCH-304FF | 14.0 | T (N, I) = 67.0° C. |
| PCH-502FF | 8.0 | $n_e$ (20° C., 589 nm) = 1.6195 |
| PCH-504FF | 14.0 | Δn (20° C., 589 nm) = 0.1254 |
| BCH-32 | 10.0 | $\epsilon_\perp$ (20° C., 1 kHz) = 7.0 |
| CCP-V-1 | 8.0 | Δε (20° C., 1 kHz) = −3.3 |
| PP-1-2V | 14.0 | $k_3/k_1$ = 0.99 |
| CC-3-V1 | 8.0 | $\gamma_1$ (20° C.) = 125 mPa·s |
| CPY-2-O2 | 12.0 | $t_{store}$ (−30° C.) > 1.000 h |
| CPY-3-O2 | 12.0 | $t_{store}$ (−40° C.) ≥ 200 h |
| Σ | 100.0 | $V_0$ (20° C.) = 2.12 V |

The present liquid-crystal mixture has a comparatively high Δn value at the same time as low rotational viscosity $\gamma_1$. In addition, this mixture has a nematic phase down to −40° C. over an extended period.

EXAMPLE 2

| Compound/ abbreviation | Concentration/ % by weight | Physical properties |
| --- | --- | --- |
| PCH-304FF | 20.0 | T (N, I) = 74.0° C. |
| PCH-502FF | 8.0 | $n_e$ (20° C., 589 nm) = 1.6131 |
| PCH-504FF | 8.0 | Δn (20° C., 589 nm) = 0.1216 |
| BCH-32 | 8.0 | $\epsilon_\perp$ (20° C., 1 kHz) = 7.4 |
| CCP-V-1 | 12.0 | Δε (20° C., 1 kHz) = −3.6 |
| PP-1-2V | 8.0 | $k_3/k_1$ = 1.08 |
| CC-3-V1 | 10.0 | $\gamma_1$ (20° C.) = 140 mPa·s |
| CPY-2-O2 | 14.0 | $t_{store}$ (−30° C.) > 1.000 h |
| CPY-3-O2 | 12.0 | $t_{store}$ (−40° C.) ≥ 1.000 h |
| Σ | 100.0 | $V_0$ (20° C.) = 2.12 V |

The present liquid-crystal mixture has a comparatively high Δn value at the same time as low rotational viscosity $\gamma_1$. In addition, this mixture also has a nematic phase at −40° C.

EXAMPLE 3

| Compound/ abbreviation | Concentration/ % by weight | Physical properties |
| --- | --- | --- |
| PCH-304FF | 12.0 | T (N, I) = 71.0° C. |
| PCH-502FF | 9.0 | $n_e$ (20° C., 589 nm) = 1.5901 |
| PCH-504FF | 11.0 | Δn (20° C., 589 nm) = 0.1068 |
| CCP-3O2FF | 12.0 | $\epsilon_\perp$ (20° C., 1 kHz) = 7.8 |
| CCH-35 | 5.0 | Δε (20° C., 1 kHz) = −4.0 |
| CC-3-V1 | 15.0 | $k_3/k_1$ = 1.05 |
| CC-5-V | 5.0 | $\gamma_1$ (20° C.) = 130 mPa·s |
| CPY-2-O2 | 12.0 | $V_0$ (20° C.) = 2.07 V |
| CPY-3-O2 | 11.0 | $t_{store}$ (−30° C.) ≥ 1000 h |
| PP-1-2V | 8.0 | |
| Σ | 100.0 | |

The present liquid-crystal mixture has a comparatively high Δn value at the same as low rotational viscosity $\gamma_1$. In addition, this mixture has a nematic phase down to −30° C. over an extended period.

EXAMPLE 4

| Compound/ abbreviation | Concentration/ % by weight | Physical properties |
| --- | --- | --- |
| BCH-32 | 9.0 | T (N, I) = 72.0° C. |
| CCP-V-1 | 10.0 | $n_e$ (20° C., 589 nm) = 1.6515 |
| CC-3-V1 | 10.0 | Δn (20° C., 589 nm) = 0.1515 |
| CC-5-V | 3.0 | $\epsilon_\perp$ (20° C., 1 kHz) = 7.6 |
| CPY-2-O2 | 12.0 | Δε (20° C., 1 kHz) = −3.7 |
| CPY-3-O2 | 13.0 | $k_3/k_1$ = 1.02 |
| B-302FF | 19.0 | $\gamma_1$ (20° C.) = 136 mPa·s |
| B-502FF | 17.0 | $t_{store}$ (−30° C.) > 1000 h |
| PP-1-2V | 7.0 | $t_{store}$ (−40 ° C.) ≥ 1000 h |
| Σ | 100.0 | $V_0$ (20° C.) = 2.19 V |

The present liquid-crystal mixture has a comparatively high Δn value at the same as low rotational viscosity $\gamma_1$. In addition, this mixture has a nematic phase at −40° C. over an extended period.

EXAMPLE 5

| Compound/abbreviation | Concentration/% by weight | Physical properties |
|---|---|---|
| PCH-304FF | 19.0 | T (N, I) = 74.2° C. |
| PCH-502FF | 4.0 | $n_e$ (20° C., 589 nm) = 1.6120 |
| PCH-504FF | 15.0 | $\Delta n$ (20° C., 589 nm) = 0.1215 |
| BCH-32 | 7.0 | $\epsilon_\perp$ (20° C., 1 kHz) = 7.6 |
| CCP-V-1 | 12.0 | $\Delta\epsilon$ (20° C., 1 kHz) = −3.8 |
| PP-1-2V1 | 8.0 | $k_3/k_1$ = 1.08 |
| CC-3-V1 | 9.0 | $\gamma_1$ (20° C.) = 154 mPa·s |
| CPY-2-O2 | 14.0 | $V_0$ (20° C.) = 2.12 V |
| CPY-3-O2 | 12.0 | $t_{store}$ (−30° C.) ≧ 1000 h |
| Σ | 100.0 | $t_{store}$ (−40° C.) ≧ 500 h |

The present liquid-crystal mixture has a comparatively high Δn value at the same as low rotational viscosity $\gamma_1$. In addition, this mixture has a nematic phase at −40° C. over an extended period.

EXAMPLE 6

| Compound/abbreviation | Concentration/% by weight | Physical properties |
|---|---|---|
| PCH-304FF | 8.0 | T (N, I) = 102.0° C. |
| PCH-502FF | 10.0 | $\Delta n$ (20° C., 589 nm) = 0.1218 |
| PCH-504FF | 12.0 | $\Delta\epsilon$ (20° C., 1 kHz) = −4.6 |
| CPY-2-O2 | 12.0 | $\gamma_1$ (20° C.) = 260 mPa·s |
| CPY-3-O2 | 12.0 | $V_0$ (20° C.) = 2.17 V |
| CCP-5O2FF | 12.0 | |
| CCP-31FF | 9.0 | |
| CCP-V-1 | 12.0 | |
| CC-3-V1 | 4.0 | |
| CBC-33 | 3.0 | |
| PP-1-2V1 | 6.0 | |
| Σ | 100.0 | |

The present liquid-crystal mixture has a comparatively high Δn value at the same as low rotational viscosity $\gamma_1$.

EXAMPLE 7

| Compound/abbreviation | Concentration % by weight | Physical properties |
|---|---|---|
| PCH-304FF | 16.0 | T (N, I) = 80.5° C. |
| PCH-502FF | 12.0 | $n_e$ (20° C., 589 nm) = 1.6175 |
| CCP-302FF | 6.0 | $\Delta n$ (20° C., 589 nm) = 0.1271 |
| CPY-2-O2 | 13.0 | $\epsilon_\perp$ (20° C., 1 kHz) = 7.1 |
| CPY-3-O2 | 12.0 | $\Delta\epsilon$ (20° C., 1 kHz) = −3.5 |
| BCH-32 | 10.0 | $k_1$ = 17.0 pN |
| CCP-V-1 | 4.0 | $k_3/k_1$ = 1.02 |
| CC-3-V1 | 9.0 | $\gamma_1$ (20° C.) = 147 mPa·s |
| CC-5-V | 7.0 | $t_{store}$ (−30° C.) > 1.000 h |
| PP-1-2V1 | 11.0 | $t_{store}$ (−40 ° C.) > 1.000 h |
| Σ | 100.0 | $V_0$ (20° C.) = 2.36 V |

EXAMPLE 8

| Compound/abbreviation | Concentration/% by weight | Physical properties |
|---|---|---|
| PCH-304FF | 16.0 | T (N, I) = 80.5° C. |
| PCH-502FF | 16.0 | $n_e$ (20° C., 589 nm) = 1.6180 |
| CCP-302FF | 7.0 | $\Delta n$ (20° C., 589 nm) = 0.1279 |
| CPY-2-O2 | 12.0 | $\epsilon_\perp$ (20° C., 1 kHz) = 7.2 |
| CPY-3-O2 | 12.0 | $\Delta\epsilon$ (20° C., 1 kHz) = −3.7 |
| BCH-32 | 11.0 | $k_1$ = 15.6 pN |
| CCP-V-1 | 4.0 | $k_3/k_1$ = 1.06 |
| CC-3-V1 | 8.0 | $\gamma_1$ (20° C.) = 163 mPa·s |
| CC-5-V | 4.0 | $t_{store}$ (−30° C. > 1.000 h |
| PP-1-2V1 | 10.0 | $t_{store}$ (−40° C.) > 1.000 h |
| Σ | 100.0 | $V_0$ (20° C.) = 2.26 V |

EXAMPLE 9

| Compound/abbreviation | Concentration/% by weight | Physical properties |
|---|---|---|
| PCH-304FF | 16.0 | T (N, I) = 81.0° C. |
| PCH-502FF | 16.0 | $n_e$ (20° C., 589 nm) = 1.6169 |
| CCP-302FF | 10.0 | $\Delta n$ (20° C., 589 nm) = 0.1265 |
| CPY-2-O2 | 12.0 | $\epsilon_\perp$ (20° C., 1 kHz) = 7.7 |
| CPY-3-O2 | 12.0 | $\Delta\epsilon$ (20° C., 1 kHz) = −4.0 |
| BCH-32 | 10.0 | $k_1$ = 16.7 pN |
| CCP-V-1 | 4.0 | $k_3/k_1$ = 1.08 |
| CC-5-V | 10.0 | $\gamma_1$ (20° C.) = 172 mPa·s |
| PP-1-2V1 | 10.0 | $t_{store}$ (−30° C.) > 1.000 h |
| Σ | 100.0 | $t_{store}$ (−40° C.) > 1.000 h |
| | | $V_0$ (20° C.) = 2.15 V |

The entire disclosures of all applications, patents and publications, cited herein and of corresponding German application No. 101 37 319.8, filed Jul. 31, 2001 is incorporated by reference herein.

What is claimed is:

1. A liquid-crystalline medium based on a mixture of polar compounds of negative dielectric anisotropy, wherein the medium comprises one or more compounds of formula I

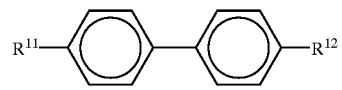

in which $R^{11}$ is an alkyl group having 1 to 12 carbon atoms or an alkenyl group having 2 to 12 carbon atoms, and $R^{12}$ is an alkenyl group having 2 to 12 carbon atoms.

2. A medium according to claim 1, further comprising one or more compounds of formula II

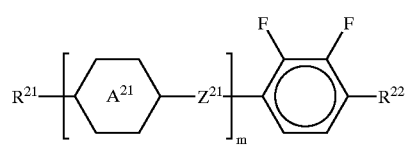

in which $Z^{21}$ is —COO— or a single bond, $A^{21}$ is trans-1,4-cyclohexylene or 1,4-phenylene, m is 1 or 2, and $R^{21}$ and $R^{22}$, independently of one another, are each an alkyl or alkenyl group having up to 12 carbon atoms, in which, optionally, one or more non-adjacent $CH_2$ groups is, in each independently, replaced by —O—, —S— or —C≡C—.

3. A medium according to claim 1, further comprising one or more compounds of formula III

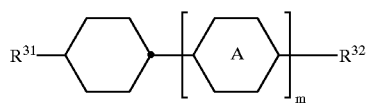

III in which ring A is trans-1,4-cyclohexylene or 1,4-phenylene, in which, optionally, one H atom is replaced by F, $R^{31}$ and $R^{32}$ are each, independently of one another, are an alkyl or alkenyl group having up to 12 carbon atoms, in which, optionally, one or more non-adjacent $CH_2$ groups is, in each independently, replaced by —O—, —S— or —C≡C—, and m is 1 or 2.

4. A medium according to claim 2, further comprising one or more compounds of formula III

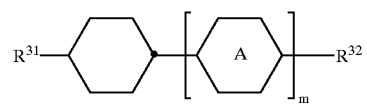

III in which ring A is trans-1,4-cyclohexylene or 1,4-phenylene, in which, optionally, one H atom is replaced by F, $R^{31}$ and $R^{32}$ are each, independently of one another, are an alkyl or alkenyl group having up to 12 carbon atoms, in which, optionally, one or more non-adjacent $CH_2$ groups is, in each independently, replaced by —O—, —S— or —C≡C—, and m is 1 or 2.

5. A medium according to claim 1, further comprising one or more compounds selected from formulae IIa to IIj

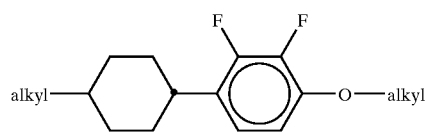

IIa

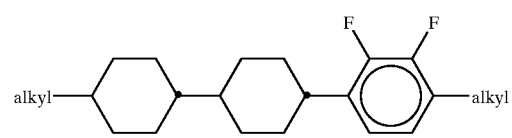

IIb

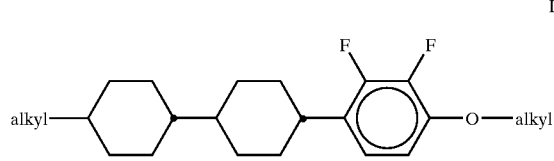

IIc

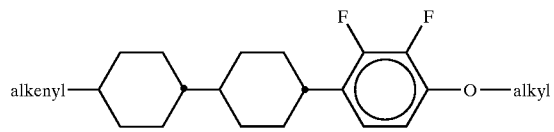

IId

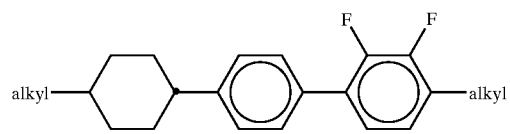

IIe

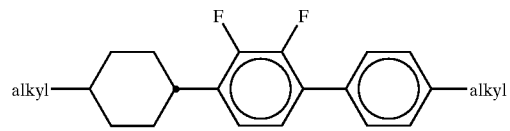

IIf

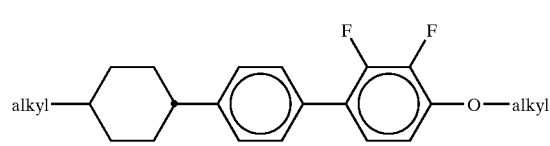

IIg

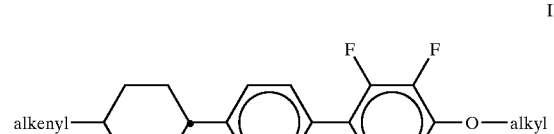

IIh

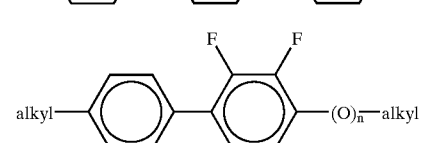

IIi

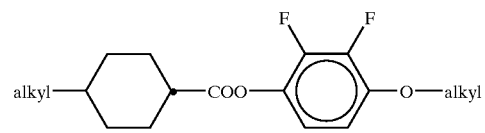

IIj in which alkyl is in each case, independently of one another, a straight-chain alkyl group having 1 to 6 carbon atoms, alkenyl is a straight-chain alkenyl group having 2 to 6 carbon atoms, and n is 0 or 1.

6. A medium according to claim 2 further comprising one or more compounds selected from formulae IIa to IIj

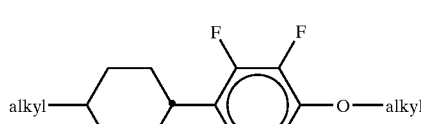

IIa

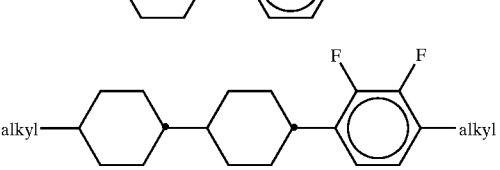

IIb

-continued

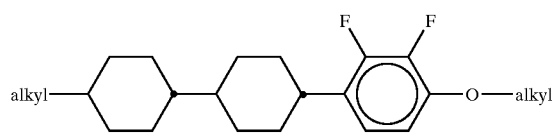
IIc

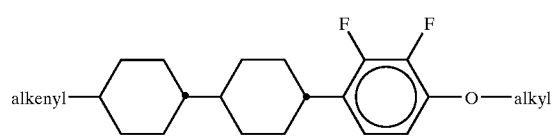
IId

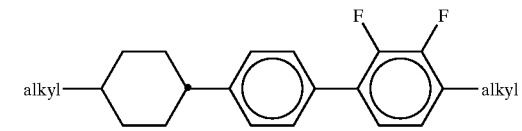
IIe

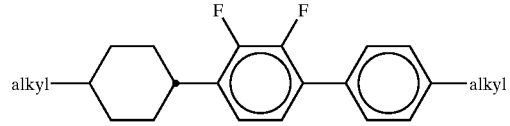
IIf

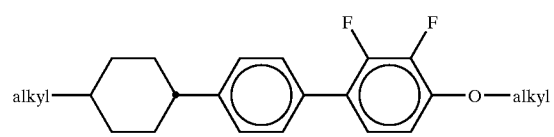
IIg

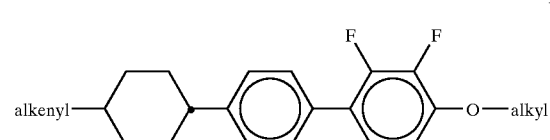
IIh

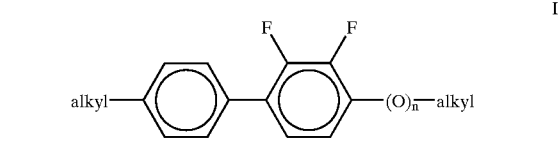
IIi

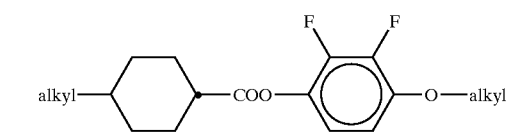
IIj

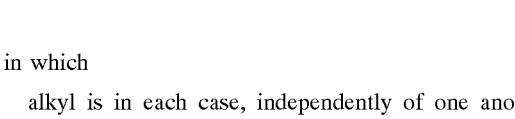

in which
- alkyl is in each case, independently of one another, a straight-chain alkyl group having 1 to 6 carbon atoms,
- alkenyl is a straight-chain alkenyl group having 2 to 6 carbon atoms, and
- n is 0 or 1.

7. A medium according to claim 3 further comprising one or more compounds selected from formulae IIa to IIj

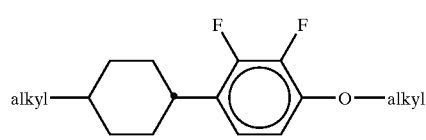
IIa

-continued

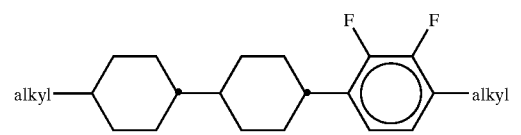
IIb

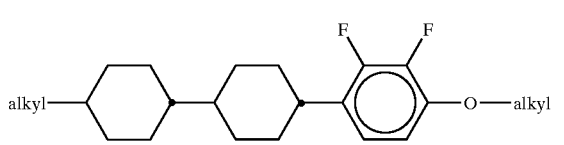
IIc

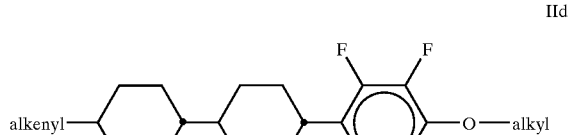
IId

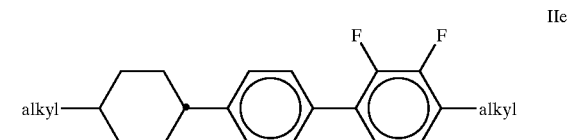
IIe

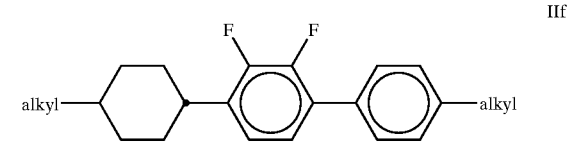
IIf

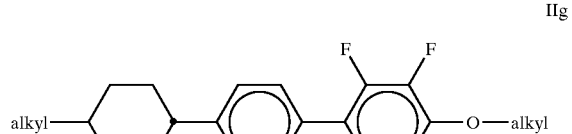
IIg

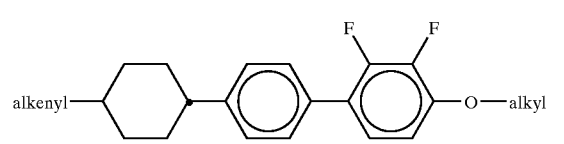
IIh

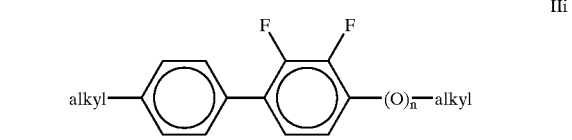
IIi

IIj in which
- alkyl is in each case, independently of one another, a straight-chain alkyl group having 1 to 6 carbon atoms,
- alkenyl is a straight-chain alkenyl group having 2 to 6 carbon atoms, and
- n is 0 or 1.

8. A medium according to claim 1, further comprising one or more compounds selected from formulae IIIa to IIIg

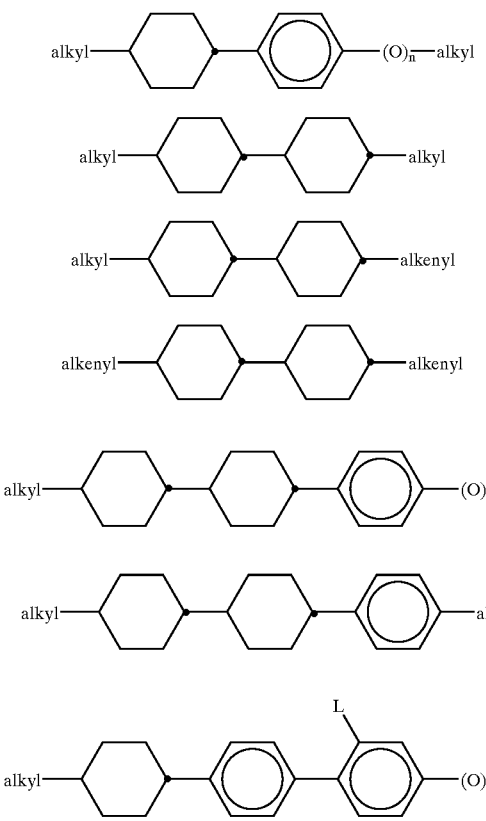

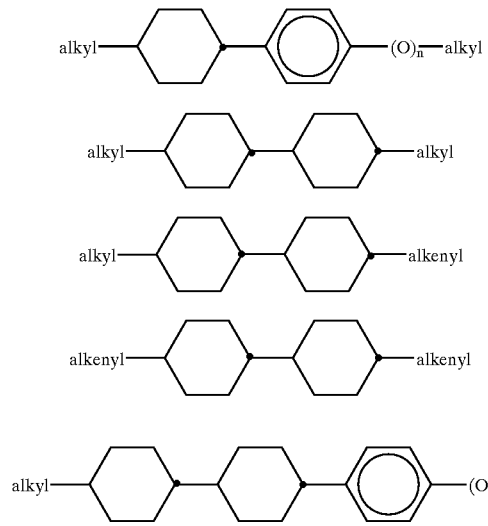

in which
- alkyl is in each case, independently of one another, a straight-chain alkyl group having 1 to 6 carbon atoms,
- alkenyl is a straight-chain alkenyl group having 2 to 6 carbon atoms,
- n is 0 or 1, and
- L is H or F.

9. A medium according to claim 1, further comprising one or more compounds selected from formulae IIIa to IIIg

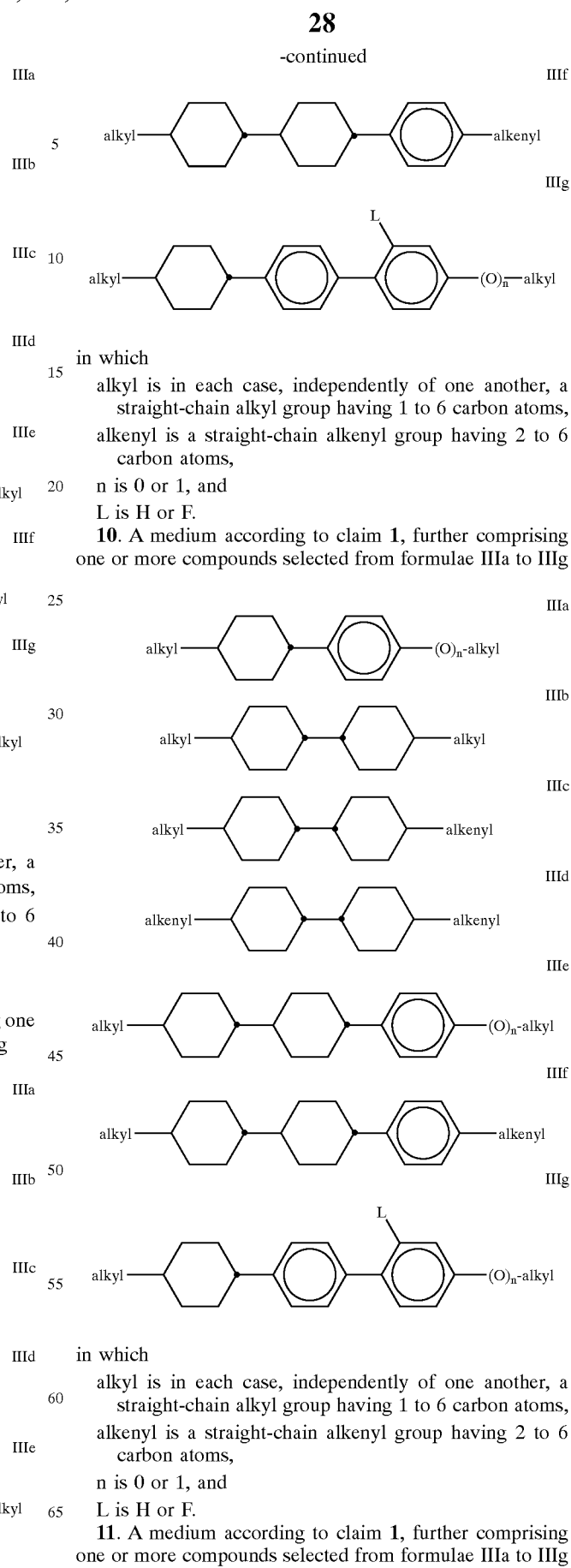

in which
- alkyl is in each case, independently of one another, a straight-chain alkyl group having 1 to 6 carbon atoms,
- alkenyl is a straight-chain alkenyl group having 2 to 6 carbon atoms,
- n is 0 or 1, and
- L is H or F.

10. A medium according to claim 1, further comprising one or more compounds selected from formulae IIIa to IIIg in which
- alkyl is in each case, independently of one another, a straight-chain alkyl group having 1 to 6 carbon atoms,
- alkenyl is a straight-chain alkenyl group having 2 to 6 carbon atoms,
- n is 0 or 1, and
- L is H or F.

11. A medium according to claim 1, further comprising one or more compounds selected from formulae IIIa to IIIg

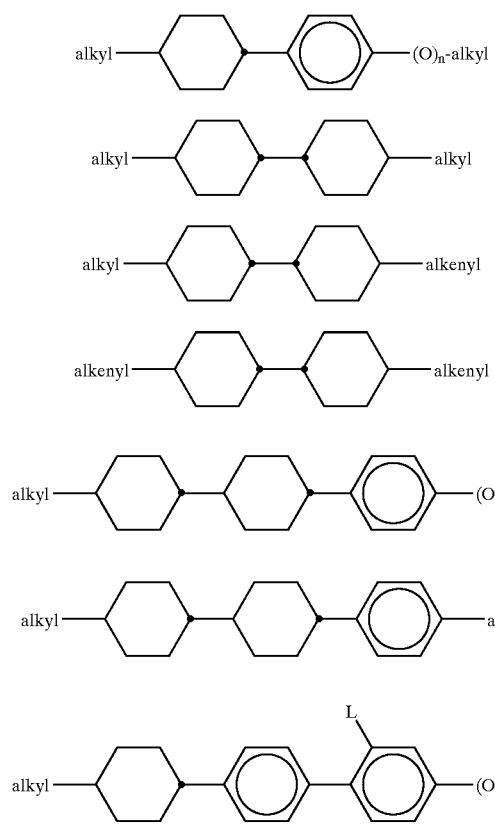

in which alkyl is in each case, independently of one another, a straight-chain alkyl group having 1 to 6 carbon atoms, alkenyl is a straight-chain alkenyl group having 2 to 6 carbon atoms, n is 0 or 1, and L is H or F.

12. A medium according to claim 4, consisting essentially of 4 or more compounds of the formulae I and II and one or more compounds of the formula III.

13. A medium according to claim 1, wherein the proportion of compounds of the formula I in the mixture as a whole is at least 10% by weight.

14. A medium according to claim 2, wherein the proportion of compounds of formula II in the mixture as a whole is at least 30% by weight.

15. A medium according to claim 3, wherein the proportion of compounds of the formula III in the mixture as a whole is at least 5% by weight.

16. A medium according to claim 4, the medium comprises

10–45% by weight of one or more compounds of the formula I,

30–85% by weight of one or more compounds of the formula II and

5–35% by weight of one or more compounds of the formula III.

17. A medium according to claim 1, further comprising one or more compounds of formula IV

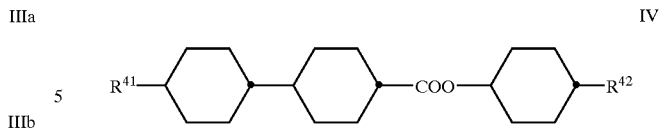

wherein $R^{41}$ and $R^{42}$, independently of one another, are each an alkyl or alkenyl group having up to 12 carbon atoms, in which, optionally, one or more non-adjacent $CH_2$ groups is, in each independently, replaced by —O—, —S— or —C≡C—.

18. A medium according to claim 1, further comprising one or more compounds of formula VI

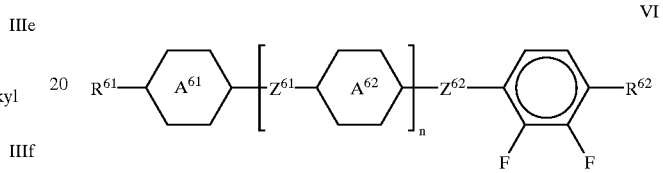

wherein $R^{61}$ and $R^{62}$, independently of one another, are each an alkyl or alkenyl group having up to 12 carbon atoms, in which, optionally, one or more non-adjacent $CH_2$ groups is, in each independently, replaced by —O—, —S— or —C≡C—,

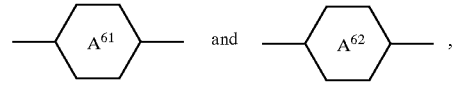

independently of one another, are

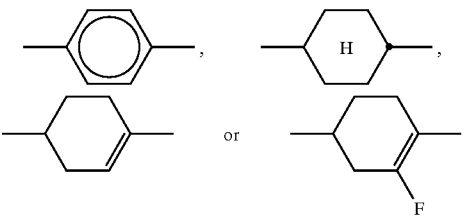

one of $Z^{61}$ and $Z^{62}$ is $OCF_2$ or $CF_2O$ and the other is a single bond, and n is 0 or 1.

19. A medium according to claim 1, further comprising one or more compounds of formula VII

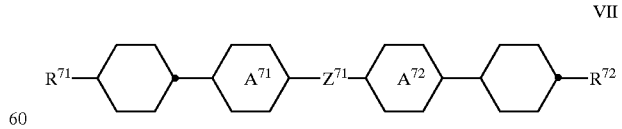

wherein $R^{71}$ and $R^{72}$, independently of one another, are each an alkyl or alkenyl group having up to 12 carbon atoms, in which, optionally, one or more non-adjacent $CH_2$ groups is, in each independently, replaced by —O—, —S— or —C≡C—, $Z^{71}$ is —CH₂CH₂—, —CH=CH—, —COO— or a single bond,

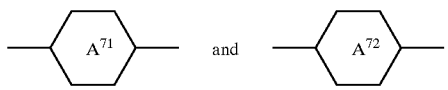 and are each, independently of one another,

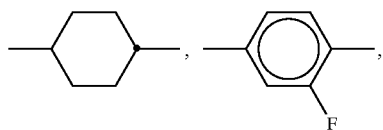,

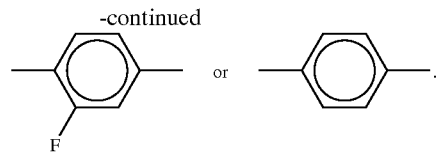

20. In an electro-optical display element, containing, as dielectric, a liquid-crystalline medium, the improvement wherein said medium is according to claim 1.

21. An electro-optical display element according to claim 17, wherein said display element is an actively addressed matrix.

22. An electro-optical display element according to claim 17, wherein said display element operates on the ECB and/or VA principle.

23. An electro-optical display element according to claim 18, wherein said display element operates on the ECB and/or VA principle.

* * * * *